(12) United States Patent
Helmy

(10) Patent No.: US 8,632,589 B2
(45) Date of Patent: Jan. 21, 2014

(54) IOL INSERTION SYSTEM WITH SEMI-AUTOMATIC TRAILING HAPTIC CONFIGURATION MANAGEMENT

(75) Inventor: Ahmed Helmy, Granada Hills, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 428 days.

(21) Appl. No.: 12/773,653

(22) Filed: May 4, 2010

(65) Prior Publication Data

US 2011/0276054 A1 Nov. 10, 2011

(51) Int. Cl.
*A61F 2/16* (2006.01)
*A61F 9/00* (2006.01)

(52) U.S. Cl.
USPC ............................ 623/6.12; 606/107

(58) Field of Classification Search
USPC .......................... 606/107; 623/6.12
See application file for complete search history.

(56) References Cited

U.S. PATENT DOCUMENTS

| | | |
|---|---|---|
| 5,616,148 A | 4/1997 | Eagles et al. |
| 5,772,666 A | 6/1998 | Feingold et al. |
| 6,022,358 A | 2/2000 | Wolf et al. |
| 2004/0116937 A1 | 6/2004 | Portney |
| 2008/0033449 A1 | 2/2008 | Cole et al. |
| 2008/0058830 A1* | 3/2008 | Cole et al. ............... 606/107 |
| 2009/0318933 A1 | 12/2009 | Anderson |

OTHER PUBLICATIONS

International Search Report and Written Opinion for Application No. PCT/US2011/035096, mailed on Oct. 31, 2011, 13 pages.

* cited by examiner

*Primary Examiner* — Thomas McEvoy
*Assistant Examiner* — Sarah W Aleman
(74) *Attorney, Agent, or Firm* — Abbott Medical Optics Inc.

(57) ABSTRACT

A system and method for performing an ocular surgical procedure is provided. The system is configured to provide an IOL having a trailing haptic to an eye and includes a pair of interlockable telescoping elements, having generally an inner and outer component configured to hold the IOL and be brought together into a locking position, the locking position maintaining the trailing haptic in an advantageously altered orientation. The system also includes a plunger configured to receive force and transmit the force to the IOL and the trailing haptic in the advantageously altered orientation.

17 Claims, 12 Drawing Sheets

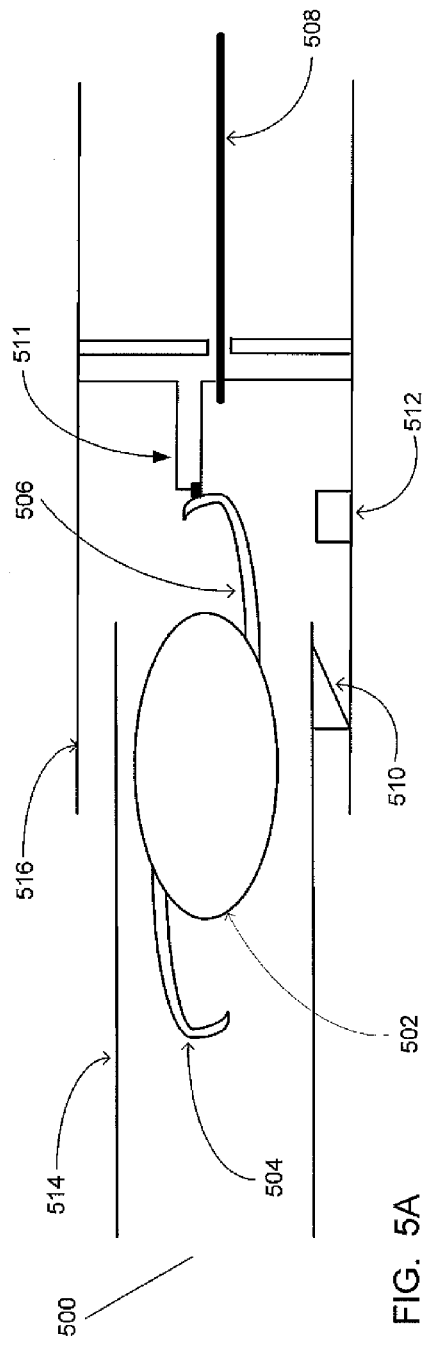
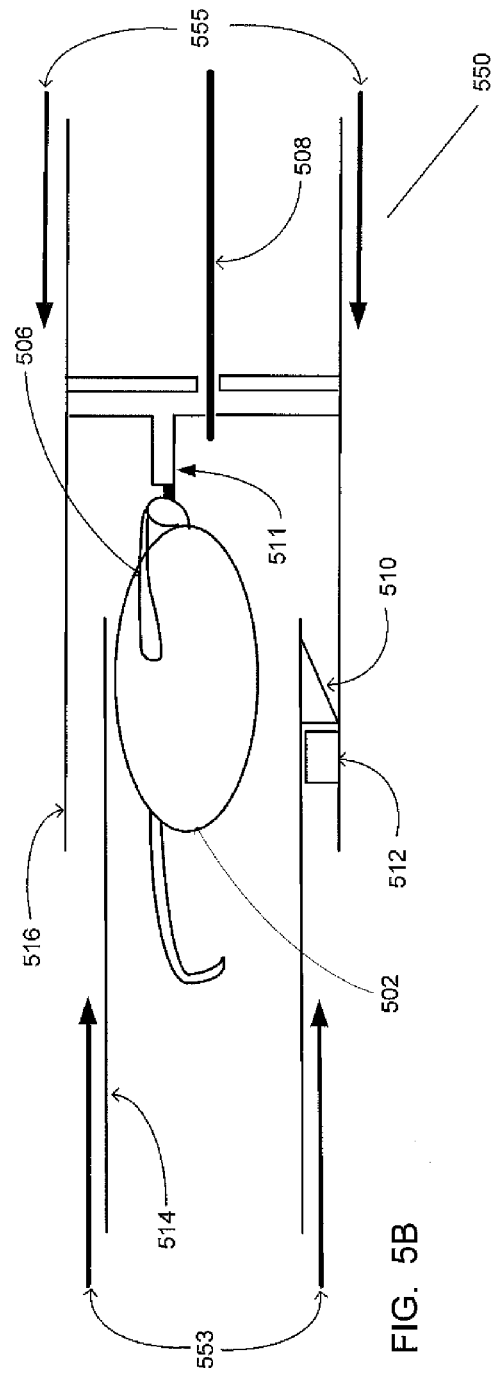
FIG. 5A
FIG. 5B

IOL INSERTION SYSTEM WITH SEMI-AUTOMATIC TRAILING HAPTIC CONFIGURATION MANAGEMENT

BACKGROUND OF THE INVENTION

1. Field of the Invention

The present invention relates generally to ocular surgery, and more specifically to an intraocular lens (IOL) insertion systems.

2. Description of the Related Art

Phacoemulsification surgery has been successfully employed in the treatment of certain ocular problems, such as cataracts, and typically entails removing a cataract-damaged lens and implanting an intraocular lens, or IOL. Phacoemulsification surgery involves removal of the cataract damaged lens utilizing a small incision at the edge of the cornea. Through the small incision, the surgeon creates an opening in the capsule, i.e. membrane that encapsulates the lens, and can through the opening can remove unwanted lens material and insert an IOL.

IOLs typically include a haptic or haptics, namely devices used to hold the lens in place. Current techniques for fabricating IOLs employ deformable polymeric materials such as acrylic, silicon, hydrogel based materials, and the like. For example, Abbott Medical Optics (AMO) of Santa Ana, Calif. manufactures a brand of aspheric IOL using a single piece of acrylic material called Tecnis®.

When performing phacoemulsification surgical techniques, such as lens insertion, the deformable polymeric materials enable the surgeon to fold, roll, and otherwise configure the IOL in a manner sufficient to position and orient the lens for placement within an eye. Once positioned and oriented, the surgeon may manually deliver the configured lens from an insertion cartridge device into an injector device and ultimately to the eye through a small incision. In general, the insertion cartridge device is installed within an IOL insertion system, i.e. a separate delivery handpiece. The surgeon may introduce the IOL manually using the IOL delivery handpiece, such as through a delivery tube, in a manner similar to operating a hypodermic needle. The IOL injector device arrangement moves the IOL from a holding area, specifically a cartridge device, located within the injector. In this arrangement, the IOL is ready for implantation, and the surgeon may engage the insertion system injector device plunger component to push the IOL into the patient's eye.

The injector device may involve a preloaded injector or a reusable, limited reuse injector, or an injector configured with an IOL insertion cartridge, arranged to ensure successful ejection and unfolding of the IOL and for protecting the integrated rear or trailing haptic sufficient to prevent damage to IOL and the haptic.

The material properties of flexible acrylic IOLs are highly dependent on the size of the insertion cartridge and the ability of a surgeon to provide the precise pressure or force necessary to insert the IOL. Use of an injector device in this manner may make it easier for the surgeon to fold and manipulate the IOL and deliver the IOL through a small cartridge and through the incision while protecting the integrity of the haptics.

Haptics may include leading and trailing haptics, where the leading haptic is the first haptic inserted through the incision and the trailing haptic the second haptic passing through the incision. This may be realized through a small slit in the IOL holding area or insertion cartridge device prior to engaging the plunger to push the IOL and move the IOL from the injector for implantation into the patient's eye.

Current methods and designs may become problematic during ejection, when the IOL unfolds from the cartridge device/holding area. During this stage of the optical procedure, the IOL and/or the integrated leading and/or trailing haptics may become damaged. Trailing haptic damage is of particular concern due to the generally increased likelihood of such damage relative to damage to other parts of the IOL. Also, current designs may fail to properly manage the forces required to move the IOL from the holding area and through the injector during insertion.

Based on the foregoing, it would be beneficial to offer a single handpiece design for operating a manual IOL insertion system configured for dynamic control of the insertion force while maintaining control of the haptic/lens configuration, where the surgeon may complete the lens replacement procedure without damaging the IOL or integrated haptics during the insertion process.

SUMMARY OF THE INVENTION

According to one aspect of the present design, there is provided a system and method for performing an ocular surgical procedure. The system is configured to provide an IOL having a trailing haptic to an eye and includes two interlockable telescoping elements, having axially similar inner and outer components, the interlockable telescoping arrangement configured to hold the IOL and be brought together into a locking position, the locking position maintaining the trailing haptic in an advantageously altered orientation. The system also includes a plunger configured to receive force and transmit the force to the IOL and the trailing haptic in the advantageously altered orientation.

These and other advantages of the present invention will become apparent to those skilled in the art from the following detailed description of the invention and the accompanying drawings.

BRIEF DESCRIPTION OF THE DRAWINGS

The present invention is illustrated by way of example, and not by way of limitation, in the figures of the accompanying drawings in which:

FIG. 5A illustrates a telescoping mechanism for configuring the trailing haptic in a first position where the IOL cartridge device is inserted into the insertion system holding area;

FIG. 5B illustrates an alternate telescoping mechanism for configuring the trailing haptic in a second position to place the trailing haptic in the desired "tucked" configuration;

DETAILED DESCRIPTION OF THE INVENTION

The following description and the drawings illustrate specific embodiments sufficient to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design is directed to manual IOL insertion, using a device such as an insertion handpiece, during an ocular procedure. The insertion handpiece arrangement may protect of the IOL and integrated leading and trailing haptics, preventing potential damage to either when the plunger is operated and pushed by the surgeon or operator. The system disclosed may include, but is not limited to, an insertion injector device in combination with a cartridge device configured with the injector device holding area for positioning the IOL prior to delivery.

The present design further includes providing for the controlling and manipulation of the IOL's leading and trailing haptics such that the IOL may be provided to the patient at an acceptable delivery force or pressure, as applied by the surgeon against the pushrod component. The present design may enable the surgeon to account for lens size, lens softness, lens flexibility, lens material type, lens diopter, IOL design configuration, cartridge device size, and management of the applied force.

While generally described herein as a manually operated insertion handpiece system, it is specifically noted that the combination of cartridge device and injector device in association with the present method and design may protect the IOL from damage during of an ocular procedure. Control and manipulation of the trailing haptic in accordance with the present design can provide for a safely controllable level of haptic deployment in conjunction with an existing phacoemulsification system.

System Example

While the present design may be used in various environments and applications, it will be discussed herein with a particular emphasis on an environment where a surgeon or health care practitioner performs. For example, one embodiment of the present design is in or with an ocular surgical system that comprises an independent graphical user interface (GUI) host module, an instrument host module, a GUI touchscreen or other visual monitoring device, and a controller module, such as a foot switch, to control the surgical system.

Figure 1:
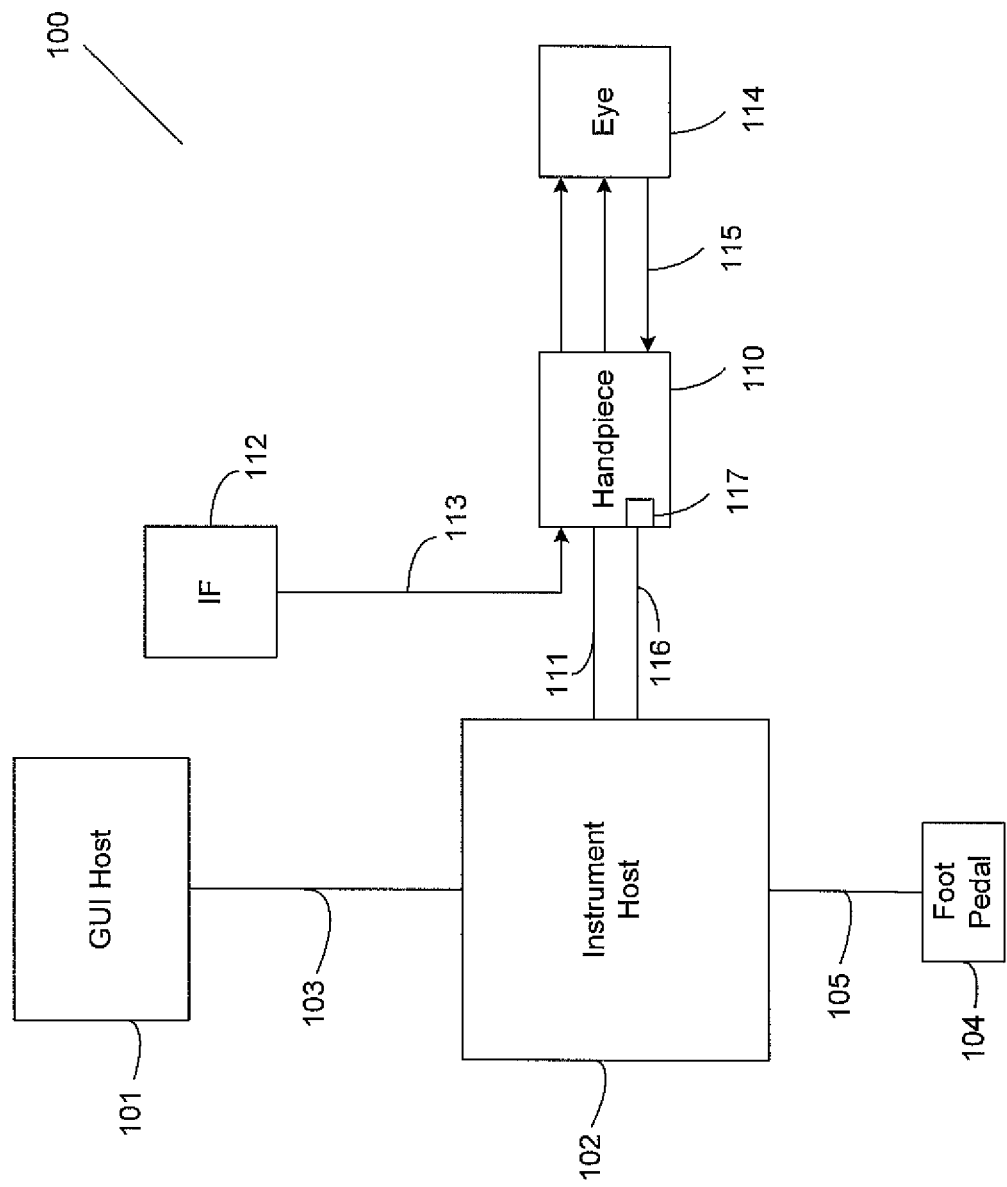
FIG. 1 illustrates an exemplary phacoemulsification/vitrectomy irrigation/aspiration system in a functional block diagram to show the components and interfaces for a medical instrument system that may be employed in accordance with an aspect of the present invention.

FIG. 1 illustrates an exemplary phacoemulsification/vitrectomy (phaco) system 100 in a functional block diagram to show the major components and interfaces for a safety critical medical instrument system that may be employed in accordance with an aspect of the present invention. A serial communication cable 103 connects GUI host or GUI host module 101 to instrument host or instrument host module 102 for the purpose of controlling the instrument host 102. Instrument host 102 may be a computer or computing device in this arrangement.

A switch module associated with foot pedal 104 may transmit control signals relating internal physical and virtual footswitch position information to the instrument host 102 over serial communications cable 105. Instrument host 102 may include a database file system for storing configuration parameter values, programs, and other data saved in a storage device (not shown). In addition, the database file system may be realized on the GUI host 101 or any other subsystem (not shown) that could accommodate such a file system.

The phaco system 100 has a handpiece 110 that includes a needle and a device, typically a piezoelectric crystal, configured to ultrasonically vibrate the needle. Instrument host 102 supplies power on line 111 to phacoemulsification/vitrectomy handpiece 110. An irrigation fluid source 112 can be fluidly coupled to handpiece 110 through line 113. The irrigation fluid and ultrasonic power are applied by handpiece 110 to an eye, or affected area or region, indicated diagrammatically by block 114. Alternatively, the irrigation source may be routed to eye 114 through a separate pathway independent of the handpiece. Aspiration is provided to eye 114 by a pump (not shown), such as a peristaltic pump, via instrument host 102, through lines 115 and 116. A surgeon/operator may select an amplitude envelope applied to each pulse via the instrument host and GUI host.

In combination with phaco system 100, the present system may enable manual control for the IOL insertion system functionality in or with the phacoemulsification system and may comprise components including, but not limited to, an ultrasonic handpiece driver and an insertion system including but not limited to an injector device, and a cartridge device position in a holding area provisioned within the injector device. The insertion system disclosed may involve either a preloaded cartridge or a preloaded injector, where the injector device design may allow for reuse. Further, the present design may involve a multiple use injector handpiece arrangement for realizing support for a single use preloaded cartridge or a device having similar functionality.

The manual control delivery functionality in the present design may operate by the surgeon advancing and retracting an IOL insertion system push rod or alternately or additionally rotating the push rod. The present design's "insertion mode or process" may provide for the movements or actions of the push rod operating within the IOL insertion system handpiece, by the surgeon performing the ocular procedure, just prior to and while in use.

Previous IOL Insertion Designs

Figure 2A:
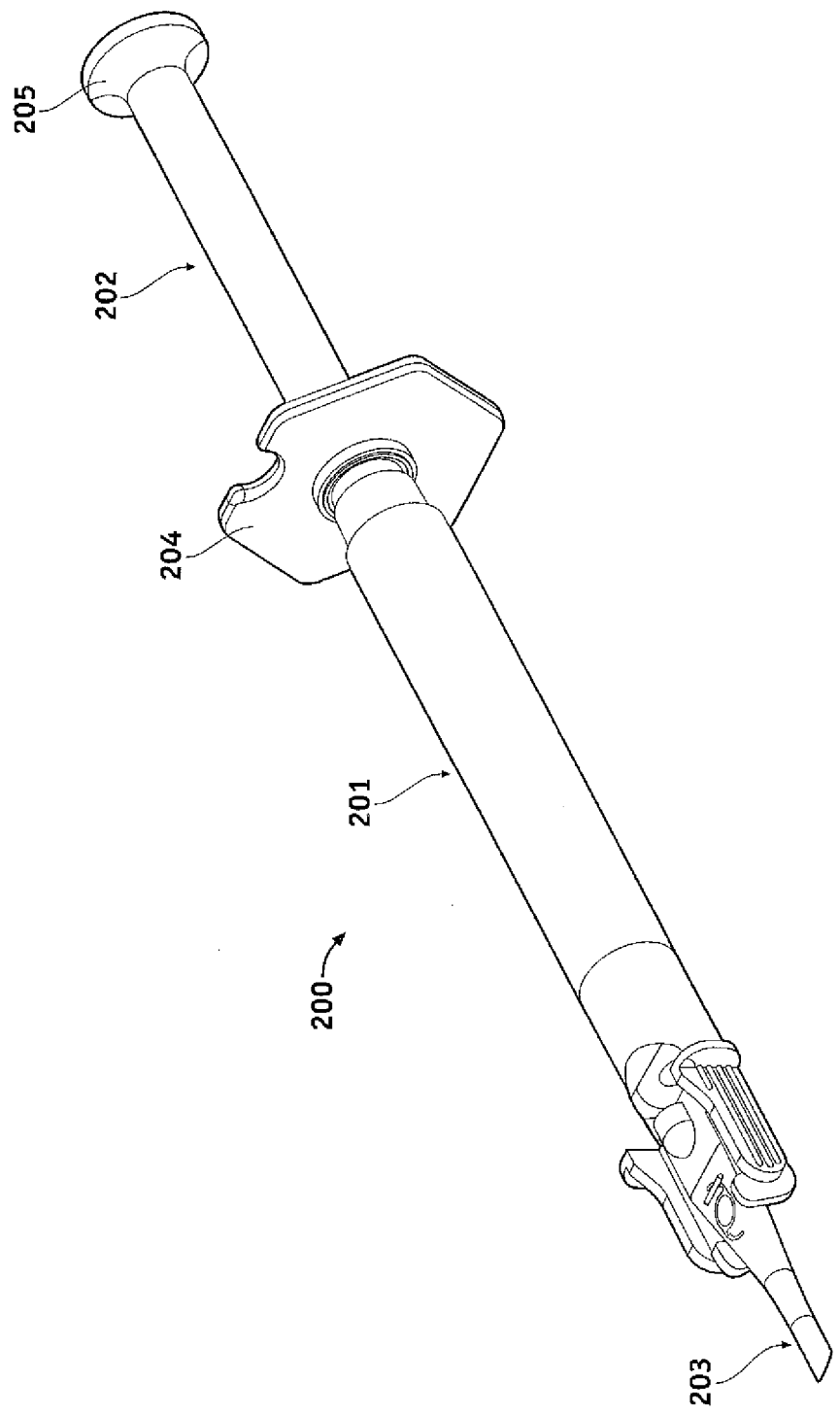
FIG. 2A shows a manual IOL injector device design.

Previous designs for providing IOLs are illustrated in FIGS. 2A through 4. FIG. 2A illustrates an exemplary arrangement for a previously available manually operated IOL insertion system 200. IOL insertion system 200 comprises a single stand-alone handpiece device or handpiece 201 as illustrated in FIG. 2A, where handpiece 201 may include plunger 202 and delivery tube 203. The surgeon operates handpiece 201 by grasping the device with a single hand at finger tab 204 and thumb cap 205. Applying force at thumb cap 205 may move plunger 202 along a longitudinal axis defined between plunger 202 and delivery tube 203 at a distal end, acting as an actuator for purposes moving the lens from delivery tube 203 through an incision into the patient's eye.

The present discussion employs the terms "force" and "pressure" under various circumstances, such as application of force to a rod or application of pressure to the rod. These terms are intended to be accorded their broadest definition and not intended to be limiting, in that the word pressure may be employed to denote force and vice versa.

Figure 2B:
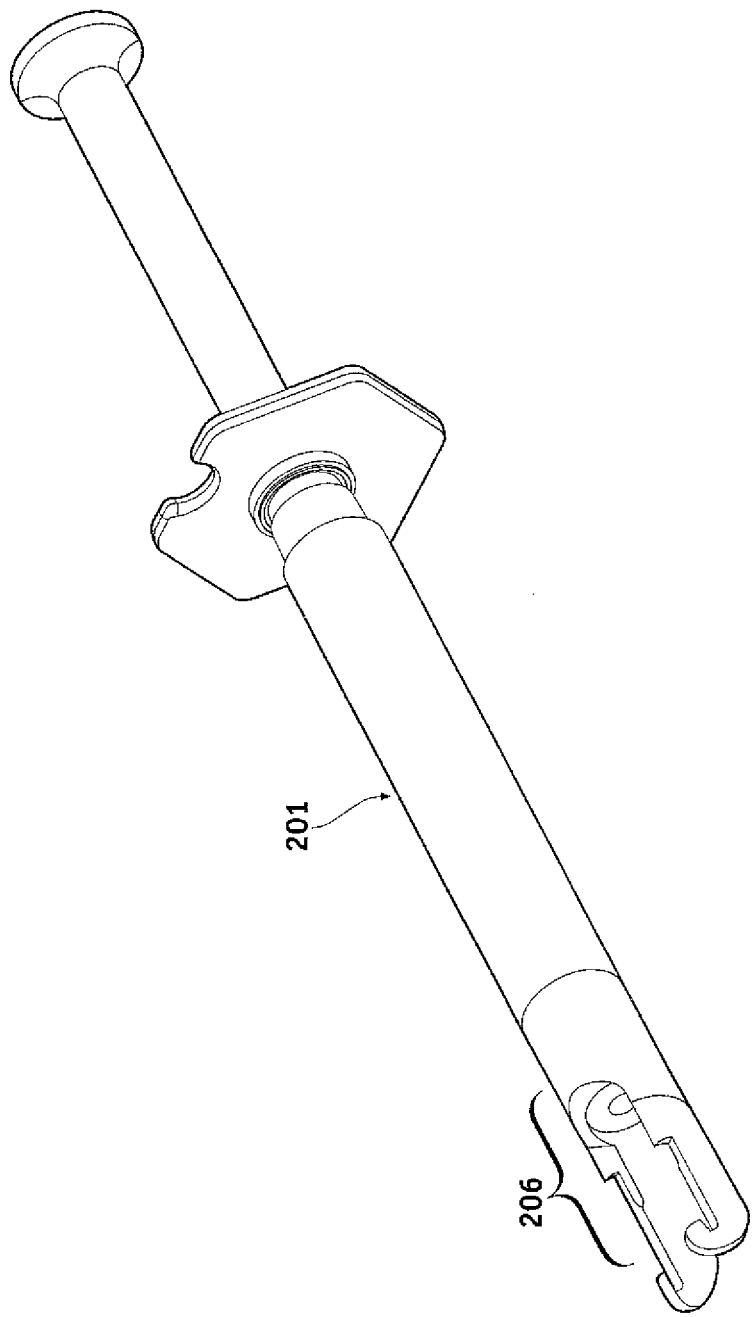
FIG. 2B illustrates a manual standalone handpiece holding station arrangement configured to receive an IOL insertion cartridge device.
Figure 2C:
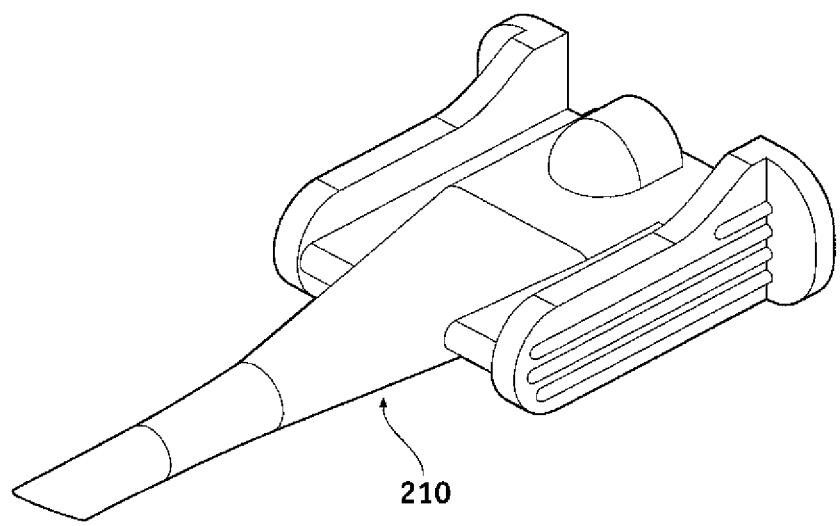
FIG. 2C illustrates an IOL manual insertion cartridge device for use with the standalone handpiece holding area located within the injector device.

FIG. 2B illustrates a holding station as part of IOL insertion system 200. Handpiece 201 comprises holding station 206 configured to receive the IOL insertion cartridge. FIG. 2C illustrates IOL insertion cartridge 210 for use with the standalone handpiece, such as holding station 206 of FIG. 2B. IOL insertion cartridge 210 comprises a new IOL optic, configured and ready for insertion into holding station 206 for use in an ophthalmic surgical procedure.

One example of an IOL manual insertion system similar to that illustrated in FIGS. 2A-2C is disclosed in U.S. patent application Ser. No. 12/144,512, "Pre-Loaded IOL Insertion System", inventor Steven R. Anderson, filed Jun. 23, 2008, the entirety of which is expressly incorporated herein.

A second example of an IOL manual insertion system similar to that illustrated in FIGS. 2A-2C is disclosed in U.S. Patent Application Publication US 2008/0033449, "Intraocular Lens Insertion Apparatus and Lens Case", inventors Mark S. Cole, et al., filed Jan. 26, 2007, the entirety of which is expressly incorporated herein. The '449 design enables the trailing haptic to be moved forward and/or "tucked" into place by the surgeon using a ViscoElastic canula tip to move the trailing haptic in relation to the IOL. The surgeon may achieve this movement and manipulation prior to delivery by accessing the trailing haptic through a small slit in the IOL holding area or insertion cartridge device. Once the IOL is placed in the desired "tucked" configuration, the surgeon may engage the plunger to push the IOL and move the IOL from the injector device for realizing delivery and implantation into the patient's eye.

Figure 3:
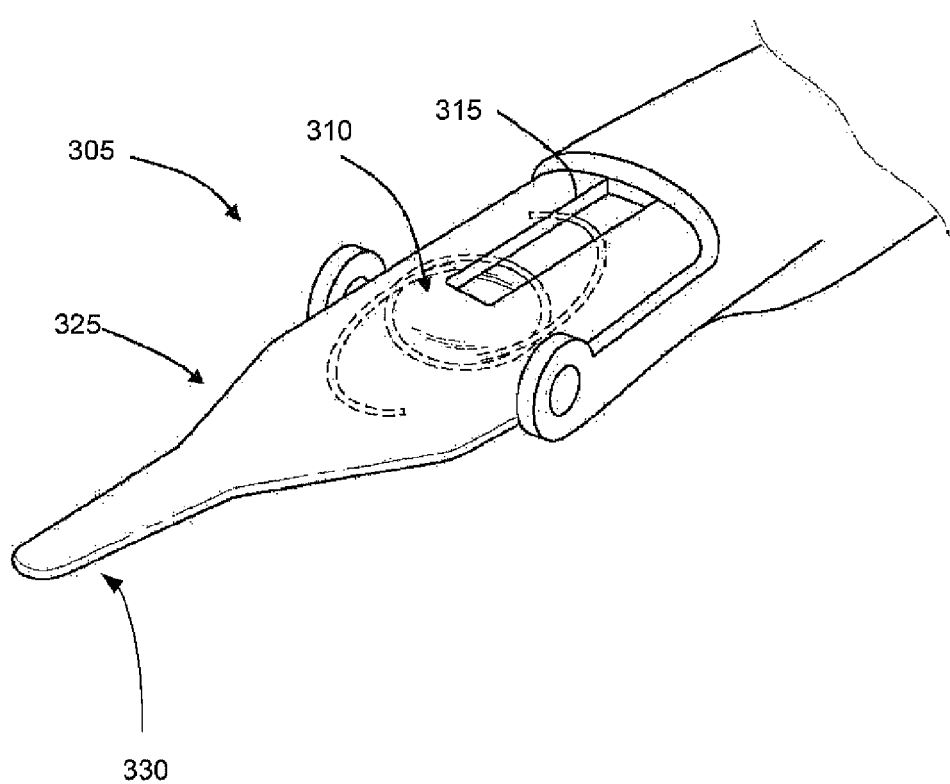
FIG. 3 is a perspective view of an inserter showing an intraocular lens disposed for insertion into the eye of a subject.

FIG. 3 shows an IOL insertion system 305 where intraocular lens 310 may be observed positioned in the load chamber through opening 315. The surgeon or operator may visually inspect the inside of cartridge 320 before, during, or after transfer of the intraocular lens into nosepiece 325. Opening 315 may also be used to introduce one or more substances, such as a viscoelastic or balanced saline solution, into the load chamber. Opening 315 may also operate as an overflow port through which excess fluids may exit the load chamber. Further, the opening may receive inspection instruments or tools for manipulating or otherwise preparing the intraocular lens for delivery through delivery tube 330.

Figure 4A:
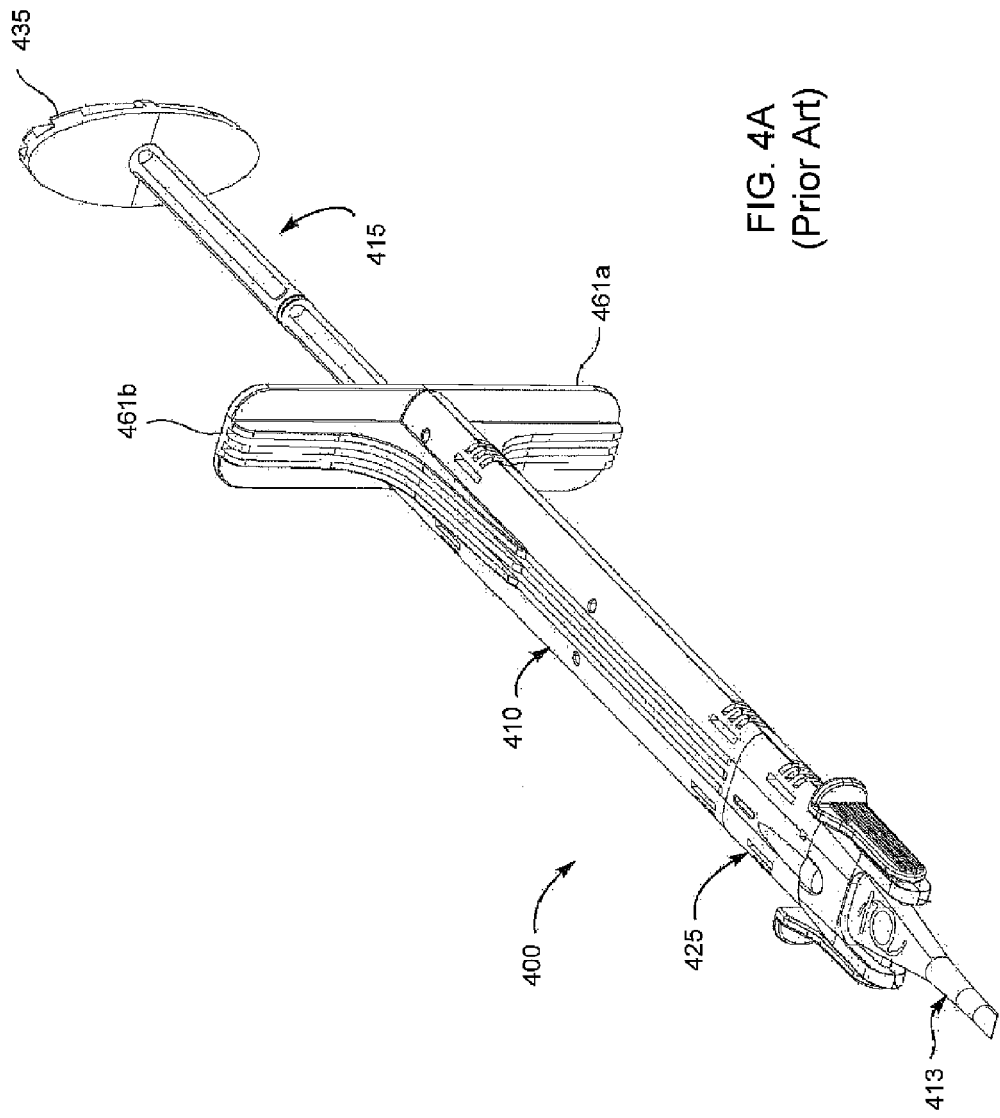
FIG. 4A is an assembled perspective view of an insertion system.

FIG. 4A illustrates an exemplary IOL insertion system 400 arrangement for a previously available manually operated system involving a syringe-style device including a handpiece 410, a plunger 415, and a delivery tube 413 on a distal end thereof. The system 400 is also shown in exploded view in FIG. 4B, with handpiece 410 and plunger 415 components also shown.

Figure 4B:
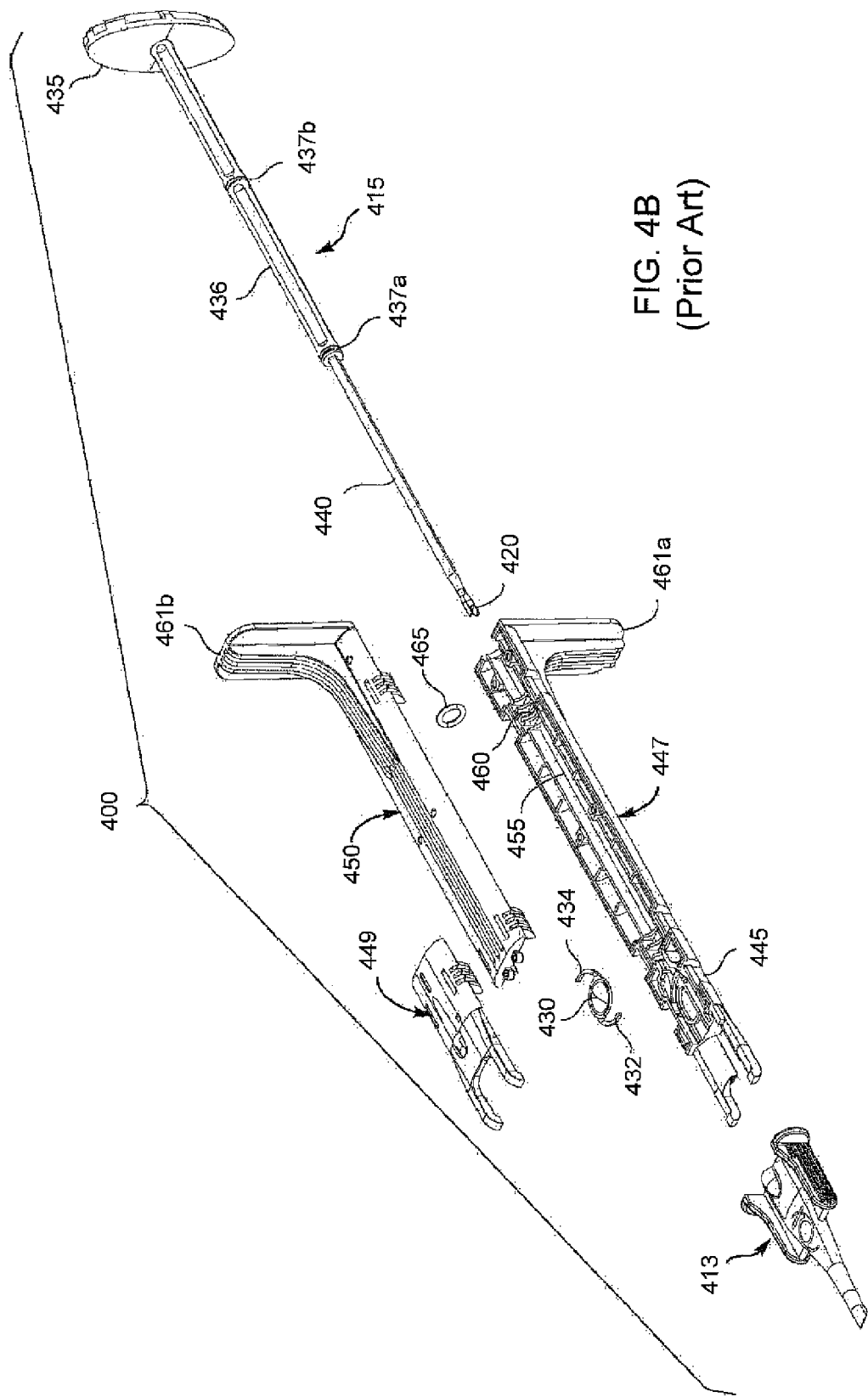
FIG. 4B is an exploded perspective view of the insertion system of FIG. 4A.

The IOL is shown in FIG. 4B and is positioned between two halves of a holding station 425. The IOL may comprise a central circular optic 430 having a leading haptic 432 and a trailing haptic 434 generally spirally extending therefrom. One exemplary IOL as illustrated is a one piece acrylic Tecnis® brand of aspheric IOL available from Abbott Medical Optics of Santa Ana, Calif.

With reference to FIGS. 4A and 4B, the system 400 defines a single longitudinal axis (not shown) from the plunger 415 at a proximal end to the delivery tube 413 at a distal end. The plunger 415 includes a thumb cap 435, a piston rod 436, a narrower push rod 440 fixedly connected to and extending from the piston rod, and a distal tip 420. In the illustrated embodiment, the distal tip 420 is forked to enable reliable capture of a proximal edge of the IOL optic 430. The plunger 415 translates axially through an elongate passage defined within the inserter handpiece 410 and is configured to expel the IOL from a holding station 425 through the distal delivery tube 413.

In a general sense, the plunger 415 represents any actuator capable of displacing the IOL from the holding station 425 in a distal direction through a delivery tube or other such device. The plunger 415 therefore may be considered an actuator or other "prime mover" that can perform the same function, such as a rotary actuators, threaded actuators, levers, and so forth.

The lower half of the holding station 425 includes a base 445 that forms a distal extension of a base portion 447 of the handpiece 410. The upper half of the holding station 425 includes a cover 449 that abuts a top portion 450 of the inserter handpiece 410. In the illustrated embodiment, as seen in FIG. 4A, the cover 449 and top portion 450 fit directly over the base 445 and base portion 447 to form the elongated handpiece 410. The overall shape of handpiece 410 may be somewhat flattened in a plane parallel to the interface between the upper and lower components. As seen in FIG. 4B, the IOL optic 430 is positioned approximately at a midplane of the inserter handpiece 410.

The handpiece further includes a pair of proximal finger tabs 461a, 461b, one on the base portion 447 and one on the top portion 450. When an operator desires to depress the plunger 415, he or she places the thumb of one hand on the thumb cap 435, and index and middle fingers on finger tabs 461a, 461b. Squeezing the hand closed depresses the thumb cap 435. The flattened nature of the handpiece 410 provides torque leverage so that the operator can more easily rotate the handpiece about its longitudinal axis.

The exploded view of FIG. 4B shows a central channel 455 in the handpiece base 447 for receiving the piston rod 436 and push rod 440. A similar mating channel is also provided on the underside of the handpiece top portion 450. A semi-circular groove 460 provided at the proximal end of the base 447 (and a similar mating groove on the underside of the top portion 450) receives an O-ring 465. The piston rod 436 includes two circular grooves 437a, 437b spaced along its length that register with the O-ring 465. Specifically, the piston rod 436 has an outer diameter slightly larger than the inner diameter of the O-ring 465, while the grooves 437a, 437b each have an outer diameter that is the same or approximately the same as the inner diameter of the O-ring.

As the piston rod 436 passes through the proximal end of the handpiece 410 it spreads apart the O-ring 465 resulting in a degree of friction between plunger 415 and the handpiece 410, damping of the movement of the piston rod 436 and/or the IOL. The O-ring 465 resiliently springs inward into each of the grooves 437a, 437b as they reach the proximal end of the handpiece. The grooves 437a, 437b and associated O-rings thus provide detents to movement of the plunger 415 through the handpiece 410.

The system 400 is packaged with the plunger 415 retracted and the distal groove 437a operating in association with O-ring 465. A technician or other user can prepare the system for an IOL insertion operation by applying the appropriate amount of a viscoelastic, manipulating the trailing haptic 434 as described below, and advancing the plunger 415 such that the proximal groove 437b registers with the O-ring 465. This positive position indicator notifies the user that the system 400 is ready for the surgeon. The plunger 415 remains out of contact, or just touches, the IOL.

Simpler configurations may be realized. The handpiece top portion 450 could be formed along with the remainder of the handpiece, though the mold would be fairly complicated and expensive. Likewise, the delivery tube 413 could be incorporated into the handpiece 410.

Current methods and designs may become problematic when in use by the surgeon or operator as a result of the ejection and unfolding of the IOL from the cartridge device/holding area. During this stage of the optical procedure, the IOL and/or the integrated leading and trailing haptics may become damaged. Proper management of the forces required to move the IOL from the holding area and through the injector device is complex, i.e. that point where the IOL is ejected into the patient's eye.

As the size of the tube of the insertion cartridge device is reduced, the delivery force required for implantation increases, which in certain situations can be problematic for the surgeon to control. Further, surgeons must limit the size of the IOL chosen based on currently available insertion systems, which is undesirable. Using an under-sized or reduced size lens may limit the effectiveness of the entire lens replacement procedure and thus may not provide the patient with optimal or desired correction.

Trailing Haptic Management

The present design moves the trailing haptic into a predetermined desired configuration prior to insertion. This configuration may enable the surgeon to control and manipulate the trailing haptic by use of a telescoping mechanism, incorporated within the IOL insertion system as disclosed herein, where the telescoping mechanism may involve a locking mechanism. The locking mechanism arrangement may involve a protrusion in the body of the handpiece back-end and cartridge loading area front-end to form a mating or latching/locking arrangement. This mating or latching/locking arrangement may operate with a sliding aspect in a telescoping configuration where the front end may be moved toward the back end, by the surgeon, to engage and lock the two components together.

This arrangement, when engaged, may enable the surgeon to manage the trailing haptic protrusion into a tucked position prior to the surgeon engaging a plunger to move the IOL. This can enable maintaining the IOL's trailing haptic during the optical implantation procedure when ejecting the IOL from the cartridge device and delivering the IOL through the cartridge device and into the patient's eye.

The surgeon may employ locking by moving the front end and back end components together, i.e. toward one another, by applying forces in an opposite direction. When the telescoping mechanism is placed in the locked position, for example by use of a pin and a latch component disposed within the insertion system, the present design may "tuck" the trailing haptic into a desired orientation, ready for implantation. The insertion system is now prepared for the surgeon to engage the plunger to push the IOL and move the IOL from the cartridge device, through the injector device, and into the patient's eye, completing the ocular procedure delivery process.

Upon removal of the natural lens using phaco system 100, typically via emulsification of said lens, known by those skilled in the art, the eye is ready for receiving the new IOL. IOLs commonly involve an optic and at least one haptic extending from the IOL for attaching the IOL within the patient's eye. The haptic or haptics allow the surgeon to fix and center the optic, sufficient for securing the IOL position, within the patient's eye during the implantation procedure. Generally, IOL construction involves a leading and trailing haptic where the surgeon may attach each haptic to the patient's eye allowing the IOL optic to focus light onto the retina, thus modifying the patient's vision.

The present design can provide for control and management of the IOL and the trailing haptic prior to IOL insertion as generally illustrated in FIGS. 5A and 5B. FIGS. 5A and 5B illustrate the associated movement for IOL plunger 511 and the corresponding telescoping action occurring when the surgeon operates the handpiece from a first position, i.e. storage, to a second position, i.e. delivery.

FIG. 5A illustrates the telescoping mechanism in the first position where the IOL cartridge device has been placed in the insertion system holding area. In the preferred embodiment, the present design may enlist a cradle designed to receive the IOL's convex shape and hold the IOL in place while operating the handpiece and tucking the trailing haptic. Initially, the IOL insertion system may be placed in a first position where the IOL and haptics are in an unstressed or undeformed condition as realized when the surgeon installs the IOL cartridge device into the insertion system holding area. FIG. 5B illustrates the telescoping mechanism in the second position for realizing a "tucked" trailing haptic placed in a desired orientation ready for delivery.

After the surgeon has positioned and secured the IOL cartridge device within the holding area portion of the insertion system, i.e. first position, the surgeon may operate the IOL insertion system by moving the front end of the insertion system towards the back end of the insertion system, by applying forces in opposite directions, until a locked arrangement is obtained. In the locked position, the IOL insertion system transitions to the second position (FIG. 5B), and the IOL can be moved from the cartridge device through the tube 514 by the surgeon actuating the insertion system push rod.

Locking in this manner places the trailing haptic in a tucked position for lower risk delivery into the patient. The telescopic insertion system in combination with the front-end to back-end locking mechanism can advantageously prepare the IOL and haptics for delivery where the trailing haptic is arranged mechanically for protection when being transported to the patient. The trailing haptic is "tucked" into a desired delivery configuration, enabling the surgeon to more accurately and precisely manage the forces, i.e. linear, rotational, and any combination thereof about the rod's linear axis. This enables the IOL to be ejected from the cartridge device toward the distal end of the injector device and pushes the IOL through the incision and into the ocular cavity. FIGS. 5A and 5B illustrate one general implementation, and other implementations are possible.

Referring to FIG. 5A, in the first position, IOL 502, leading haptic 504, and trailing haptic 506 are shown in an unstrained or relaxed condition. The first position results when the surgeon inserts the IOL insertion system cartridge device into the injector device's holding area. In this configuration, the surgeon has not yet prepared the IOL and integrated haptics for implantation. Plunger 508 is illustrated in the maximum retracted position, resulting in IOL plunger 511 also being retracted, and the locking mechanism is arranged in a disengaged configuration. The locking position is realized using two components. The first component, latch 510, is shown to the left of the second component, locking pin 512. In the first position, shown in FIG. 5A, the front end 514 of the telescoping mechanism (514, 516) is extended furthest from the back end 516 such that the two ends are at maximum separation. Although the embodiment illustrated shows a latch and locking pin arrangement, the locking mechanism may be any mechanism including an o-ring, a lock washer, and other devices suitable for realizing the locking mechanism functionality.

FIG. 5B illustrates the design in the second position. The second position is realized by operating the telescoping mechanism to engage the locking mechanism by bringing the front piece 514 toward the back piece 516. The locked configuration may be established by the surgeon applying forces to move the front end 514, in direction shown by the arrows at point 553, toward the back end 554, in direction shown by the arrows at point 555, engaging latch 510 with locking pin 512. FIG. 5B illustrates latch 510 located to the right of locking pin 512 achieving the locked position.

In this configuration IOL plunger 511 engages the IOL trailing haptic and pushes the haptic into a tucked arrangement. The telescoping mechanism places the IOL 502, ready for implantation, in a stressed condition, in relation to the first position, and trailing haptic 506 is "tucked." In short, the surgeon may slide the front end toward the back end to lock the telescoping mechanism and operates IOL plunger 511. In order to move the IOL and complete the insertion process, the surgeon may operate plunger 508 sufficient to eject the IOL from the distal end of the injector device, with the "tucked" haptic being transmitted to the patient via the surgical site.

In general, the telescoping member may take any shape, including but not limited to concentric cylindrical members, or generally flat members such as the designs shown in FIGS. 4A and 4B, or an irregular shape, or any other appropriate form based on the function performed. The device generally includes two members sharing a common axis, wherein bringing the members together results in the members of whatever shape sliding along the axis and in certain instances interlocking such as in the manner shown in FIG. 5. It is to be understood that while a locking mechanism is shown in FIGS. 5A and 5B, no such interlock is required, and interlocking may be provided in other ways including but not limited to locking rims, pins, or tabs, or other mechanical locking arrangements known to those skilled in the art.

The present construction of the entire arrangement, including the front end and back end, may include materials suitable for interaction with the IOL to preserve desired shelf life characteristics for storing the IOL. For example, the front end may be fabricated from materials such as polypropylene, polyurethane, or other suitable materials with a lubricious surface that does not negatively interact with the IOL material. The lubricious surface may include, but is not limited to, a balanced salt solution (BSS) or similar fluid, a viscoelastic or ophthalmic viscoelastic device in combination with the BSS. Lubricating the IOL by filling or partially filling the cartridge with a lubricant in this manner may reduce friction and protect the IOL and integral haptics from damage when manipulating and operating the present design.

The back end may include materials such as polypropylene, polysulfone or ultem material, and certain metals. The polypropylene embodiment is well suited for a single use disposable device application. The polysulfone or ultem material can be employed in a limited re-use device application. A metal fabrication may employ either stainless steel, such as a 316 stainless steel, or titanium.

Manual IOL Delivery

Figure 6:
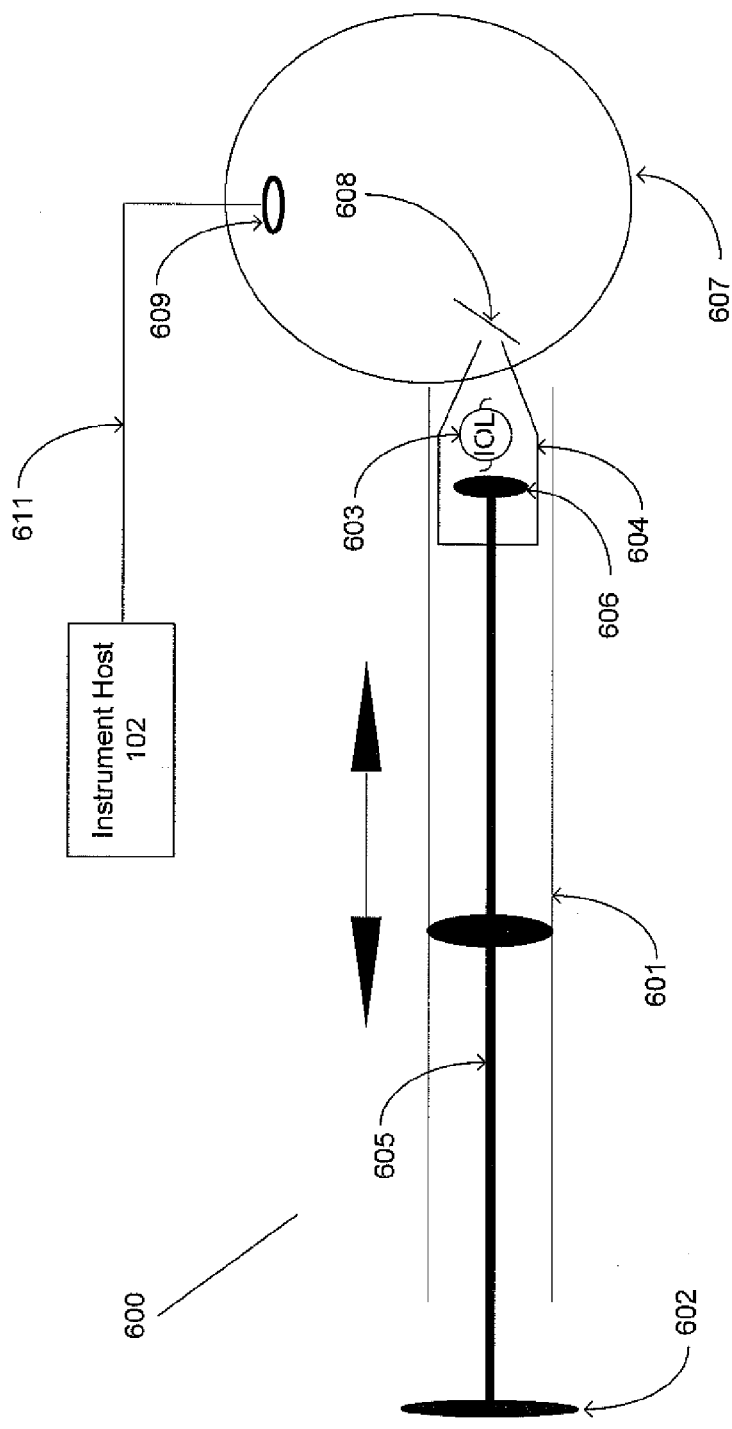
FIG. 6 illustrates a generalized view of an exemplary insertion system delivery arrangement for use in IOL implantation ocular procedures.

FIG. 6 illustrates a generalized view of an exemplary IOL insertion system for use in IOL implantation ocular procedures in accordance with an aspect of the present design. The FIG. 6 representation illustrates a simplified rendering, for purposes of disclosure, that combines the telescoping IOL insertion system handpiece 500 shown in a pre-stressed position in FIG. 5A and insertion system handpiece 550 shown in a stressed position in FIG. 5B, and may include a sleeve or exterior 601, thumb cap 602, IOL 603, cartridge 604, and rod 605 with proximal end 606. From FIG. 6, rod 605 may be a single rod or may take other forms, including but not limited to a round base or flat round disk having the rod attached to the center thereof to enable force application over a wide area, or a multiple rod arrangement. Rod 605 may be moved laterally and or torqued, or combinations thereof to effectuate delivery of IOL 603 from cartridge device 604 to eye 607 through incision 608.

The present design may provide for greater control over the insertion process. The system may afford enhanced control in manipulating IOL 603 and may facilitate insertion using a smaller incision size as compared with current designs. The present design may be employed with insertion systems involving an injector device in conjunction with a cartridge device, deployed with IOLs using either a pre-loaded or a hand-loaded arrangement.

FIG. 6 illustrates the major components, devices, interfaces, and interactions for an exemplary IOL insertion system 600. The surgeon may input the desired linear and rotational forces by manually activating push rod 605 via thumb cap 602. Force may be provided along a longitudinal axis, moving the IOL from tube 601. The surgeon may provide alternate forces, such as a rotational force, or torque, along the same longitudinal axis. Such rotational force may move the IOL from a chamber or cartridge device 604, i.e. positioned within the holding area (not shown), separately or in combination with the linear force in a manner sufficient to rotationally and/or linearly transfer the lens into the patient's eye during an implantation procedure.

The handpiece may include a holding station similar to that shown at point 301 of FIG. 3. An insertion cartridge comprises a new IOL optic 603, configured for insertion into holding area or station (not shown). In an optional configuration, the surgeon may place a pressure sensor 609 to monitor the intraocular pressure within the patient's eye, where pressure sensor 609 may communicate measured data to instrument host 102 via communications connection 611. Use of such a pressure sensor can enable relatively smooth delivery of the IOL to the patient in association with the telescoping mechanism or arrangement disclosed herein.

In summary, the surgeon may provide the lens with greater control than previously available designs. Using the present design may allow surgeons to apply greater delivery forces through smaller sized incisions and with lower risk of haptic damage, improving procedure outcomes resulting in shorter healing times and fewer complications.

Systems illustrated in FIG. 1 through 6 simply show components and devices that may be used within the present design. The size and shape of the components illustrated are not to scale nor accurately sized. Further, more or fewer components may be included in the system than are shown in the figures depending on the circumstances and implementation of the present designs insertion system configuration with transfer mechanism.

Operational Use

Figure 7:
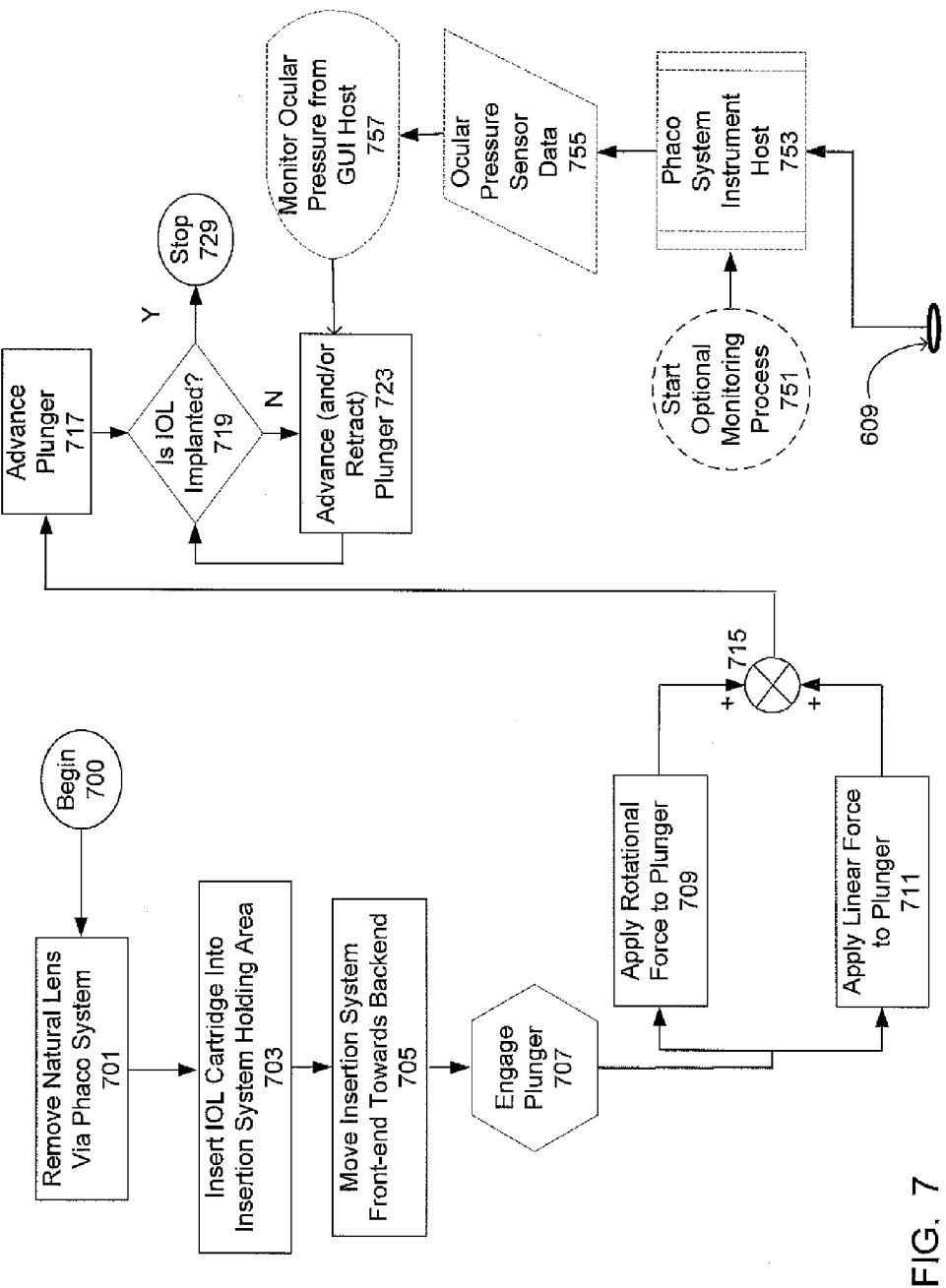
FIG. 7 is a flowchart illustrating general operation of the IOL Insertion system for implantation of an IOL.

FIG. 7 is a flowchart illustrating general operation of the IOL insertion system. The method illustrated in FIG. 7 may begin with the surgeon operating the phaco system at point 701 to remove the natural lens from the patient's eye. Typically, the ultrasonic capabilities afforded by the phaco system at point 701 may allow the surgeon to emulsify the natural lens such that it may be removed using an irrigation and aspiration process which is well known by those skilled in the art. In certain situations, the surgeon may elect to leave the natural lens in the eye, where the IOL is inserted and used in combination with the natural lens to refract light and focus the light on the retina. In other situations, more than one IOL may be implanted with the eye, depending on the type of ocular correction required.

Once the patient's eye is ready for implantation, the surgeon may insert an IOL cartridge device into the insertion system holding area at point 703. When the IOL is loaded into the insertion system, the surgeon may operate the telescoping mechanism disclosed by moving the front end toward the back end, as shown in FIG. 5B, to "tuck" the trailing haptic into a configuration to decrease risk of harm to the patient and IOL during the ocular implantation process. The surgeon may then operate the injector device's plunger at point 707, inducing a rotational force at point 709 and or a linear force at point 711 and combinations thereof, wherein the present design may combine or sum the forces at point 715. Inducing forces advances the plunger as shown at point 717. The system may then deliver the IOL from the distal end of the IOL insertion system to the patient's eye, resulting in a successful implantation procedure at point 719. This produces a 'yes' condition at point 727 and the surgeon may stop the procedure at point 729. In the situation where the IOL is not yet completely delivered or implanted, the present design may produce a 'no' condition and the surgeon may continue the procedure at point 723. The surgeon may continue to advance or retract the plunger at point 723 until the IOL is deemed as successfully implanted.

In combination with the IOL insertion system, the present design may be optionally arranged with the phacoemulsification/vitrectomy (phaco) system 100, illustrated in FIG. 1, where phaco system 100 may be configured to monitor the ocular region to measure the force applied based on the monitored ocular pressure sensed within the patient's eye, via pressure sensor 609 shown in FIG. 6.

In essence, the present design may provide feedback, for example via GUI host 101, illustrated in FIG. 1, by sensing the amount of pressure encountered in delivering the IOL to the eye and providing an indication of the measured ocular pressure to the surgeon via the GUI host display component. In this configuration, the surgeon may be able to determine a reasonable amount of force to apply on the IOL or rod to deliver the IOL quickly and conveniently to the eye.

During operational use, the surgeon may want to start monitoring the optional monitoring process, i.e. intraocular pressure, at point 751. Phaco system instrument host at point 753 software may receive and process signals relating dynamically measured operating values, in near real-time, and provide the values in the form of reported ocular sensor data at point 755 to GUI host at point 757 for display, for example, but not limited to, pressure values as measured from pressure sensor 609. The surgeon may view the GUI display presentation at point 757 to monitor, observe, and track actual ocular pressure characteristics for purposes of feedback during the procedure. For example, based on measured readings from the processed signals measured at the pressure sensor, the surgeon may decide to either advance or retract the plunger at point 723 to operating rod 605, shown in FIG. 6, component of the insertion system handpiece to increase or decrease the amount of torque or linear force applied to the rod.

The present design thus provides for control and monitoring of selected ocular characteristics during IOL implantation including but not limited to delivery force, IOL delivery speed, and allows adjustments for diopter, IOL design and dimensions, cartridge size, and data collected from within the ocular region. The present design may provide feedback to the surgeon from instrument host 102, shown in FIG. 1, sufficient for the surgeon to adjust the delivery means or delivery mode by advancing/retracting the rod, and or rotating the rod to deliver the IOL. Data on selected variables, such as diopter, IOL design (including number and type of haptics), and so forth, may be maintained in a database or computed based on known equations.

For example, if a certain diopter IOL requires an additional amount of pressure as compared with a standard diopter, that amount may be employed for presentation to the surgeon, for example via GUI Host 101, shown in FIG. 1, to determine and graphically present a range of acceptable intraocular pressures desirable during the application of forces to the system push rod or plunger. In this configuration the present design may allow larger delivery forces and delivery rates controllable by the surgeon.

In a further embodiment, the surgeon may choose to use or modify the values, stored and maintained within the database, prior to during conduct of the ocular implant procedure to seek to obtain a smooth delivery of the IOL, or the system may calculate forces based on the values input and information available.

Rather than forcing the IOL into the ocular region at a high rate or only partially, hesitantly, or incompletely delivering the IOL through the incision, the present device provides for the surgeon to apply a relatively even pressure delivery profile for the IOL using the present designs push rod or plunger design. In this arrangement, the present device may provide the surgeon an efficient and effective means for managing the delivery speed when applying pressure to the rod or similar device during the delivery process and provide the IOL through the incision.

Movement of the rod may take varying forms. In addition to the movements described above, the rod may advance and retract, where retraction is employed under specific conditions. Turning or rotating of the rod may be provided, and the IOLs may be pushed or pulled depending on desired performance under the conditions encountered. Control may be provided via the surgeon as discussed herein. For example, the surgeon may retract or pull the rod in instances where an excessive amount of force is encountered while delivering the IOL, and a problem condition may be indicated from measured intraocular pressure.

Figure 8:
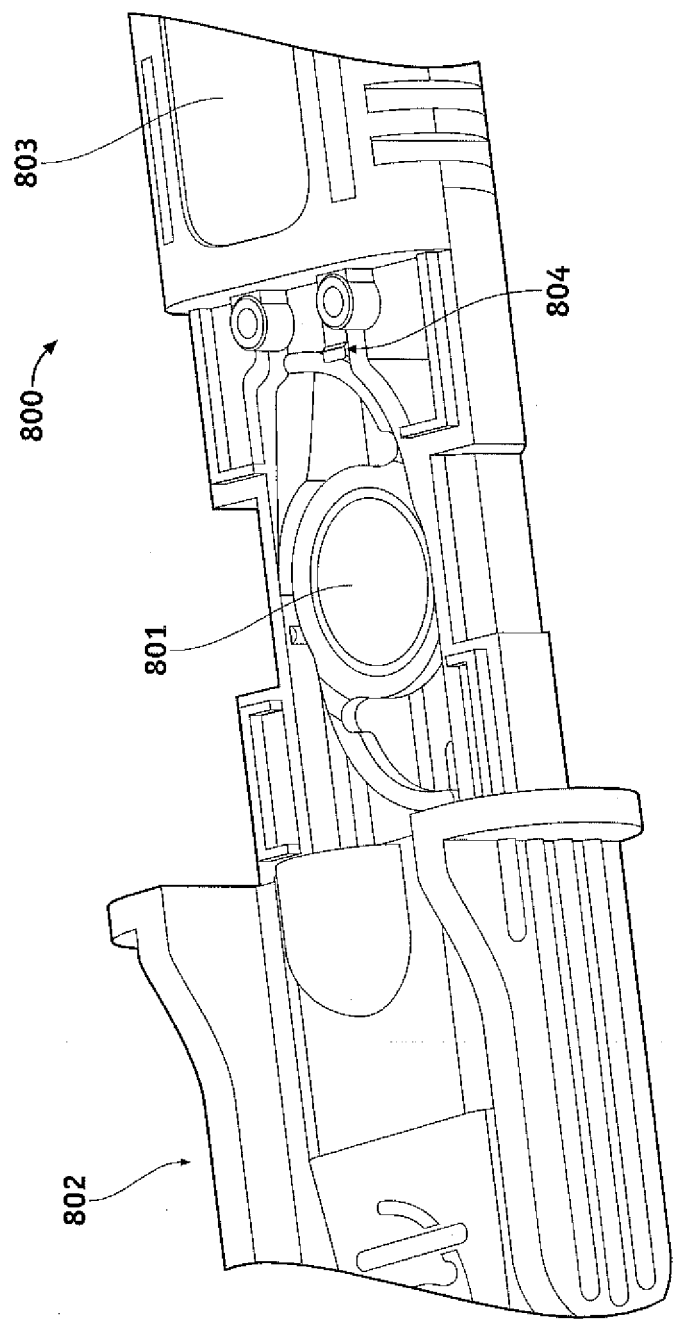
FIG. 8 illustrates an embodiment of the present design.

FIG. 8 illustrates a further embodiment of the present design. IOL 801 includes leading and trailing haptics and is mounted within the IOL inserter 800 as shown. Delivery tube 802 may be grasped by the operator and holding station 803 may be pulled toward delivery tube 802, thereby causing the forward piece 804 of the plunger to deform the trailing haptic of IOL 801 in a manner as suggested in FIG. 5B. A locking mechanism (not shown) may be provided to enable delivery tube 802 to interconnect or interlock with holding station 803, resulting in a "locked and loaded" configuration.

Figure 9:
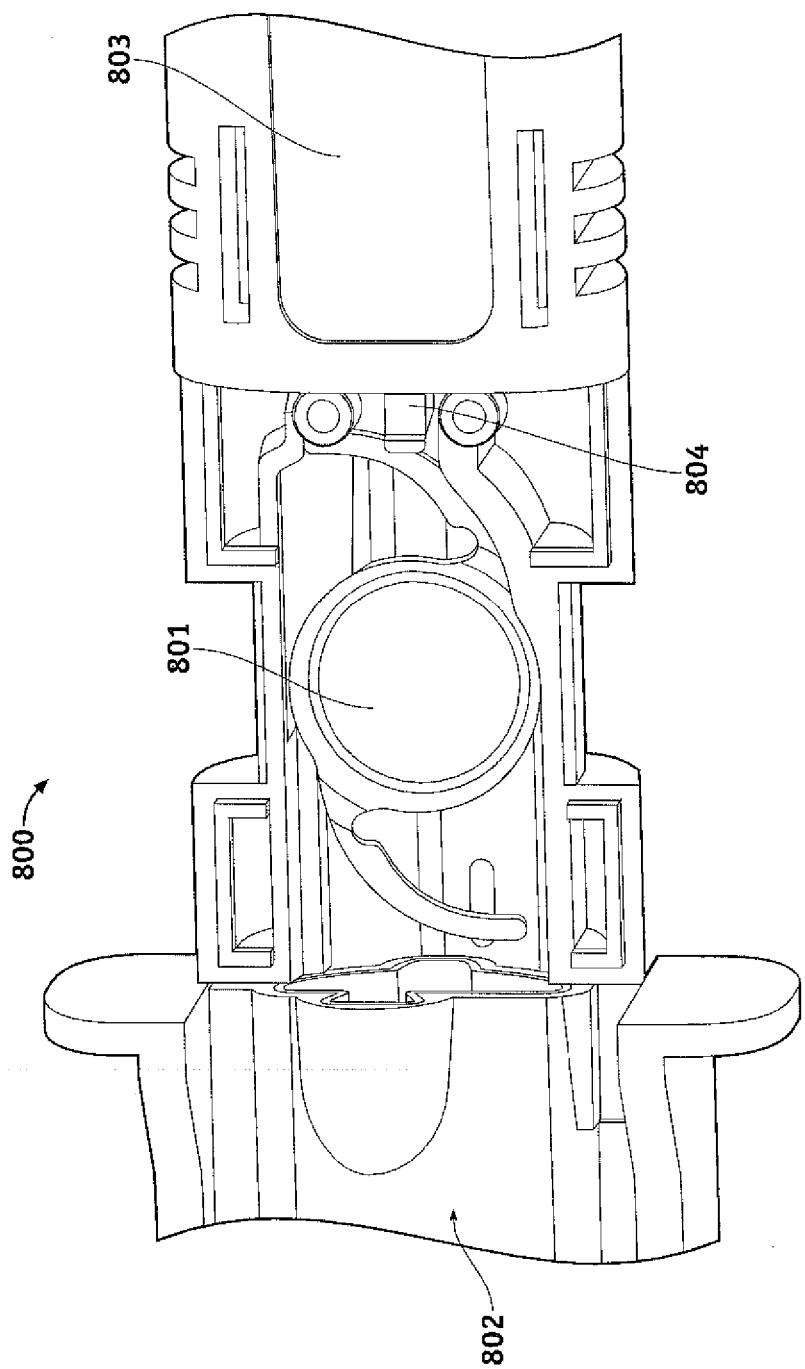
FIG. 9 shows an alternate view of the embodiment of FIG. 8, including a loaded IOL with leading and trailing haptics and a forward piece of a plunger set to deform the trailing haptic to an advantageous loading orientation.

FIG. 9 illustrates an alternate view of the device of this embodiment, including IOL inserter 800, IOL 801, delivery tube 802, holding station 803, and forward piece 804.

The IOL insertion device may be configured to receive an IOL in a preloaded cartridge or in a preloaded configuration. Alternately, the IOL insertion device may be configured to be loaded with the IOL prior to insertion. As a further alternative, the IOL insertion device may comprise a limited reuse injector component configured to maintain the IOL.

In short, the present design may provide for manually operated or powered IOL insertion affording control over high delivery forces and providing manually induced linear and rotational forces to move the rod within an IOL insertion system delivery handpiece during the lens implantation surgical procedures, using a telescoping and locking design that advantageously positions the haptic of the IOL for reduced risk of harm during delivery. The system is thus configured to provide an IOL having a trailing haptic to an eye and includes two interlockable telescoping elements, the lockable telescoping arrangement configured to hold the IOL and be brought into a locking position, the locking position maintaining the trailing haptic in an advantageously altered orientation. The system also includes a plunger configured to receive force and transmit the force to the IOL and the trailing haptic in the advantageously altered orientation.

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. An IOL injector configured to provide an IOL having a trailing haptic to an eye, comprising:
    a handpiece with a distal end and a proximal end;
    a holding area in the handpiece comprising a front piece located toward the distal end of the handpiece and a back piece located toward the proximal end of the handpiece;
    a plunger configured to pass through the holding area; and
    a delivery tube located on the distal end of the handpiece;
    wherein the front piece and back piece are coupled together in a lockable telescoping arrangement and configured to receive the IOL in an unstressed state and place the IOL in an advantageously altered stressed state such that when the front piece and back piece are brought together into a locking position, the plunger engages the trailing haptic of the IOL and places it in the advantageously altered stressed state; and wherein the locking position maintains the trailing haptic in the stressed state.

2. The IOL insertion system of claim 1, further comprising a cartridge configured to receive the IOL, wherein the cartridge fits with one of two generally cylindrical elements.

3. The IOL insertion system of claim 1, wherein locking causes the trailing haptic to be deformed toward the IOL.

4. The IOL insertion system of claim 1, wherein the lockable telescoping arrangement comprises an internal latch and locking pin formed in the lockable telescoping arrangement.

5. The IOL insertion system of claim 1, wherein the plunger comprises a rod attached to a fluid force element.

6. The IOL insertion system of claim 5, wherein the plunger is configured to move generally axially within the lockable telescoping arrangement and is further configured to move rotationally within the lockable telescoping arrangement.

7. An IOL insertion apparatus configured to provide an intraocular lens (IOL) with a trailing haptic to an eye, comprising:
    an injector device comprising a holding area comprising a front piece and a back piece;
    a cartridge device configured to maintain the IOL with the trailing haptic, the cartridge device fitting within the holding area of the injector device; and
    a pushrod device configured to operate within the injector device to expel the IOL from the cartridge device and into the eye;
    wherein the front piece and back piece are coupled together in a lockable telescoping arrangement and configured to move from an unlocked first position to a locked second position when the front piece and back piece are brought together, wherein the first position is configured to receive an IOL in an unstressed state and the IOL is then advantageously altered into a stressed state in the second position by the pushrod which engages the trailing haptic of the IOL.

8. The IOL insertion apparatus of claim 7, wherein the lockable telescoping arrangement in a locked position causes the trailing haptic to be bent toward the IOL within the injector device.

9. The IOL insertion apparatus of claim 8, wherein the lockable telescoping arrangement comprises an internal latch and locking pin formed in the lockable telescoping arrangement.

10. The IOL insertion apparatus of claim 7, wherein the pushrod device comprises a rod attached to a fluid force element.

11. The IOL insertion system of claim 7, wherein the pushrod device is configured to move generally axially within the lockable telescoping arrangement and is further configured to move rotationally within the lockable telescoping arrangement.

12. The IOL insertion system of claim 7, wherein the pushrod device is configured to be operated by a pressure generating device.

13. The IOL insertion system of claim 7, wherein the injector device is configured to operate in conjunction with a sensing device configured to sense pressure in the eye.

14. The IOL insertion device of claim 13, wherein the sensing device is configured to provide pressure data to a system configured to provide control information for the pushrod device.

15. The IOL insertion device of claim 7, wherein the IOL insertion device is configured to receive an IOL in a preloaded condition.

16. The IOL insertion device of claim 7, wherein the IOL insertion device is configured to be loaded with the IOL prior to insertion.

17. The IOL insertion device of claim 7, wherein the IOL insertion device comprises a limited reuse injector component configured to maintain the IOL.

* * * * *